United States Patent
Ohnuma et al.

[19]

[11] Patent Number: 5,875,017
[45] Date of Patent: Feb. 23, 1999

[54] OCULAR OPTICAL SYSTEM SIMULATION APPARATUS

[75] Inventors: Kazuhiko Ohnuma, Chiba; Hua Qi; Atsuo Minato, both of Tokyo, all of Japan

[73] Assignee: Hoya Corporation, Tokyo, Japan

[21] Appl. No.: 866,159

[22] Filed: May 30, 1997

[30] Foreign Application Priority Data

| May 31, 1996 | [JP] | Japan | 8-138941 |
| Aug. 16, 1996 | [JP] | Japan | 8-216223 |
| Nov. 13, 1996 | [JP] | Japan | 8-301887 |

[51] Int. Cl.$^6$ .................................................. A61B 3/00
[52] U.S. Cl. .................................................. 351/205
[58] Field of Search .................... 351/200, 204, 351/205, 216, 246; 623/6

[56] References Cited

U.S. PATENT DOCUMENTS

| 5,293,533 | 3/1994 | Klyce . | |
| 5,532,770 | 7/1996 | Schneider et al. . | |
| 5,652,640 | 7/1997 | Schneider | 351/205 |

FOREIGN PATENT DOCUMENTS

| 0 663 179 A1 | 4/1995 | European Pat. Off. . |
| A-55-147607 | 11/1980 | Japan . |
| A-63-129317 | 6/1988 | Japan . |
| 04-371912 | 12/1992 | Japan . |
| 06-341923 | 12/1994 | Japan . |
| WO 94/18636 | 1/1994 | WIPO . |

*Primary Examiner*—George Manuel
*Attorney, Agent, or Firm*—Griffin, Butler, Whisenhunt & Szupl,LLP

[57] ABSTRACT

An apparatus for simulating a retinal image obtained when a lens is used with a human eye. The apparatus can simulate intraocular lenses, contact lenses or eyeglass lenses. When intraocular lenses are simulated, a lens system 31 comprises photographic lenses and an intraocular lens mounting section. The intraocular lens is held within one or more liquid containing sections provided in the intraocular lens mounting section. The relative position of the photographic lenses and the intraocular lens is set by making the paraxial object point distance of a front refracting face of the intraocular lens substantially equal that calculated when the intraocular lens replaces a crystalline lens of Glustrand's ocular model. When simulating contact or eyeglass lenses, a front face of a lens disposed nearest the object in lens system 31 has substantially the same radius of curvature as that of a human cornea, and a contact lens supporting base has a shape corresponding to the conjunctiva of the eye. An image of the object 30 formed by the lens system 31 thus designed is captured by a CCD camera 32 and the image is then displayed on a display unit 33.

16 Claims, 3 Drawing Sheets

OCULAR OPTICAL SYSTEM SIMULATION APPARATUS

FIELD OF THE INVENTION

The present invention relates to an ocular optical system simulation apparatus for simulating a retinal image when an intraocular lens is implanted in the eye, or when a contact lens or an eyeglass lens is worn on or with the eye.

BACKGROUND OF THE INVENTION

It is difficult for an observer to experience how a patient fitted for a device such as an intraocular lens, contact lens or eyeglass lens actually sees an object.

It is difficult for an observer to actually experience how things can be seen by a patient and various studies have been conducted in order to solve this problem. In one such study, an ocular model which allows even a person of less advanced age to experience visual characteristics, illuminated visual environment, chromatic environment and the like of a person of advanced age has been proposed (Japanese Patent Laid-Open No. 63-129317).

When visual acuity drops due to a cataract or the like, attempts have been made to recover the visual acuity of the patient by the implantation of an intraocular lens (IOL) to replace a crystalline lens whose function has been impaired. Intraocular lenses can be divided generally into mono-focus lenses having one focal point, and multi-focus lenses having a plurality of focal points. Specifically, the multi-focus lenses include double-focus lenses, triple-focus lenses, progressive multi-focus lenses and the like. Further subdivisions are also possible.

A lens suitable for a patient is selected among these various intraocular lenses.

Up until now, however, a doctor has been unable to know in advance how things would actually be seen by a patient after an intraocular lens is implanted. Likewise, the patient in whom the intraocular lens was implanted could not know in advance how things would be seen after the intraocular lens is implanted. That is, both the doctor and the patient could know only numerical data such as diopter of the intraocular lens and could not confirm, for example, properties such as scattering characteristics and contrast in advance.

Furthermore, even if the doctor wanted to check whether the intraocular lens had been implanted in the patient properly, there has until now been no other way but to ask the patient about scattering characteristics, contrast and the like, and to check the results by measuring the visual acuity by means of eyecharts and other tests.

Meanwhile, researchers and developers of intraocular lenses also could not know how things would be seen by a patient when a newly developed intraocular lens is implanted. This fact has been a big obstacle in the research and development of intraocular lenses.

Accordingly, it is an object of the present invention to solve the aforementioned problems by providing a simulation apparatus which allows a retinal image of a object when an intraocular lens is implanted to be simulated.

There has been an increase in patients in recent years who try to recover their visual acuity by wearing contact lenses in place of eye glasses when their visual acuity is lowered. Contact lenses can also be classified into single-focal lenses having one focal point per lens and multi-focal lenses having a plurality of focal points per lens. Furthermore, multi-focal lenses include, for example, bifocal lenses, trifocal lenses, progressive lens and the like, which can be further subclassified.

In the case of contact lenses, it is also required to select a suitable contact lens for a patient among these various lenses.

However, researchers or developers of such contact lenses have, like the developers of intraocular lenses, not been able to know how a patient actually sees an object with a given newly developed or proposed contact lens. This has inhibited the research and development of contact lenses. Lastly, similar problems have been encountered by the developers of eyeglass lenses, and such developers have also sought after an accurate method or apparatus of simulating the retinal image of an individual or patient wearing a particular eyeglass lens.

In view of the above problems, it is a further object of the present invention to provide an ocular optical system simulation apparatus for simulating a retinal image of a patient when a contact lens or eyeglass lens is worn.

SUMMARY OF THE INVENTION

In view of the above objects, the invention provides an ocular optical system simulation apparatus for simulating retinal images when an intraocular lens is implanted, or when contact or eyeglass lenses are worn.

In one embodiment, the invention comprises a lens system, comprising a model eye compound lens system for imitating the optics of human eyes, having an intraocular lens support for supporting a simulated intraocular lens, and an image shooting, capturing or pickup device for shooting or capturing an image formed by the lens system. The retinal image formed when the intraocular lens is implanted is simulated by mounting the intraocular lens to be simulated in the intraocular lens support.

In another embodiment of the invention, the intraocular lens support comprises one or more liquid containing sections for holding liquid that may reproduce the optical properties of the vitreous humor of the eye, wherein the simulated intraocular lens is supported in the liquid held in the liquid containing sections.

In a further embodiment, a display is provided for displaying an image shot or captured by the pickup device.

In a still further embodiment, the paraxial object point distance of a front refracting face of a simulated intraocular lens mounted in the intraocular lens supporting means is made substantially equal to a paraxial object point distance of a front refracting face of the intraocular lens when it is implanted in a human eye.

In yet another embodiment, the distance of paraxial object point of the front refracting face of the intraocular lens when it is implanted a human eye is determined by an optical system in which a crystalline lens of Glustrand's ocular model is replaced with the intraocular lens.

Also in accordance with above objects, a further embodiment of the present invention provides an ocular optical system simulation apparatus for simulating a retinal image when a contact lens is worn by a patient. The invention comprises a lens system having a human model eye optical subsystem, a simulated contact lens, and an image pickup for picking up an image focused by the lens system.

In one embodiment, the invention provides an ocular optical system simulation apparatus, wherein the human model eye optical subsystem comprises a number of lenses, and has a simulated cornea lens with a first face disposed nearest an object to be viewed. A radius of curvature of the first surface of the simulated cornea lens is substantially equal to the radius of curvature of the cornea of a human eye.

In yet another embodiment of the present invention, a liquid is filled between the first surface of the simulated cornea lens and the simulated contact lens, thereby supporting the contact lens.

In a still further embodiment, a contact lens supporting base is provided outside of an outer periphery of the simulated cornea lens. In this embodiment, a liquid is filled between the contact lens supporting base and the simulated contact lens, thereby supporting the contact lens.

In another embodiment, a part or all of the surface of the contact lens supporting base opposite to the object has substantially the shape of the conjunctiva of a human eye.

Another embodiment of the invention further comprises an image pickup, and a display for displaying an image picked up by the pickup.

Yet another preferred embodiment, the image pickup comprises a charge coupled device camera.

A still further embodiment of the invention is an apparatus for simulating an ocular optical system and for simulating a retinal image when an eyeglass lens is worn by an individual, comprising a lens system having a model eye lens subsystem for simulating a human ocular optical system, and a simulated eyeglass lens, and an image pickup means for picking up an image focused by the model eye lens system.

Further objects, features and advantages of the present invention will become apparent from the Detailed Description of the Preferred Embodiments which follows, when considered together with the attached Figures.

DETAILED DESCRIPTION OF THE PREFERRED EMBODIMENTS

Figure 1:
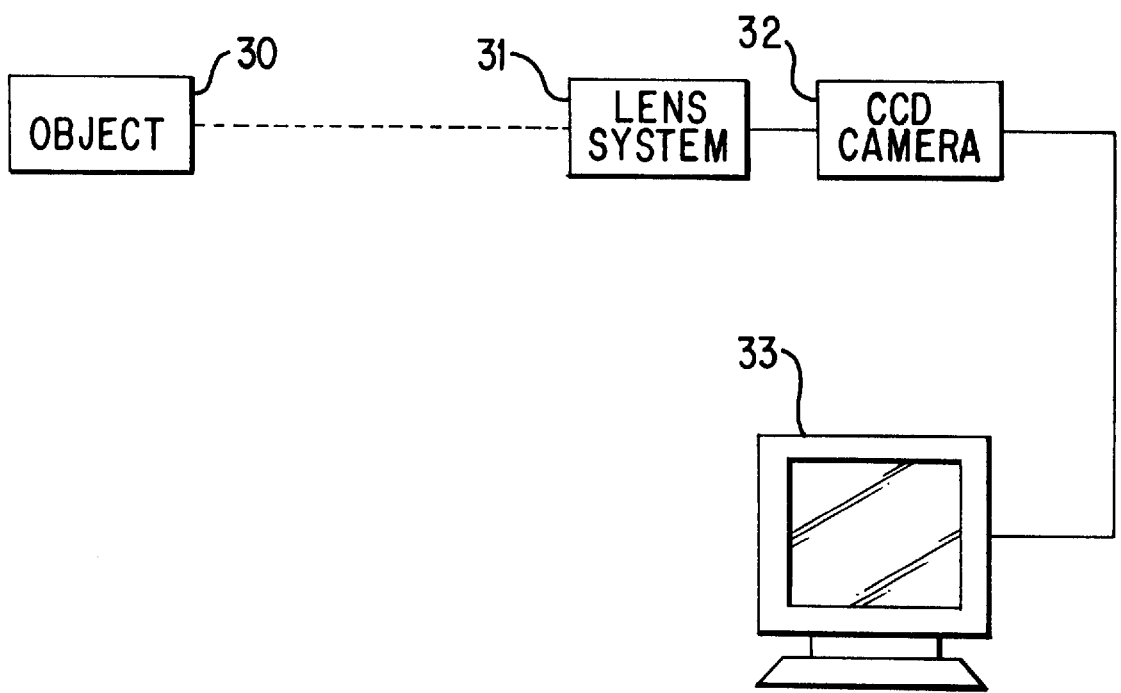
FIG. 1 is a schematic view of the ocular optical system simulation apparatus of the present invention.

Embodiments of the ocular optical system simulation apparatus according to the present invention are described in detail below with reference to the drawings, in which like parts are referred to by like reference numerals.

FIG. 1 shows a schematic structure of the ocular optical system simulation apparatus according an embodiment of the present the invention. The ocular optical system simulation system comprises a lens system 31, a pickup or CCD (charge coupled device) camera 32 and a display unit 33.

In this embodiment, the lens system 31 comprises photographic lenses, an intraocular lens and others as described later and forms an image of an object 30.

The CCD camera 32 shoots or captures the image of the object 30 via the lens system 31 and the captured image is sent to the display unit 33. The relative position of the CCD camera 32 and the lens system 31 may be varied.

The display unit 33 displays the image captured by the CCD camera 32. A color display is used in the present embodiment.

Next, the structure of the lens system 31 will be explained below in detail with respect to the first embodiment of the invention relating to the simulation of a retinal image formed by an intraocular lens.

Intraocular Lens Simulation Embodiment

Figure 2:
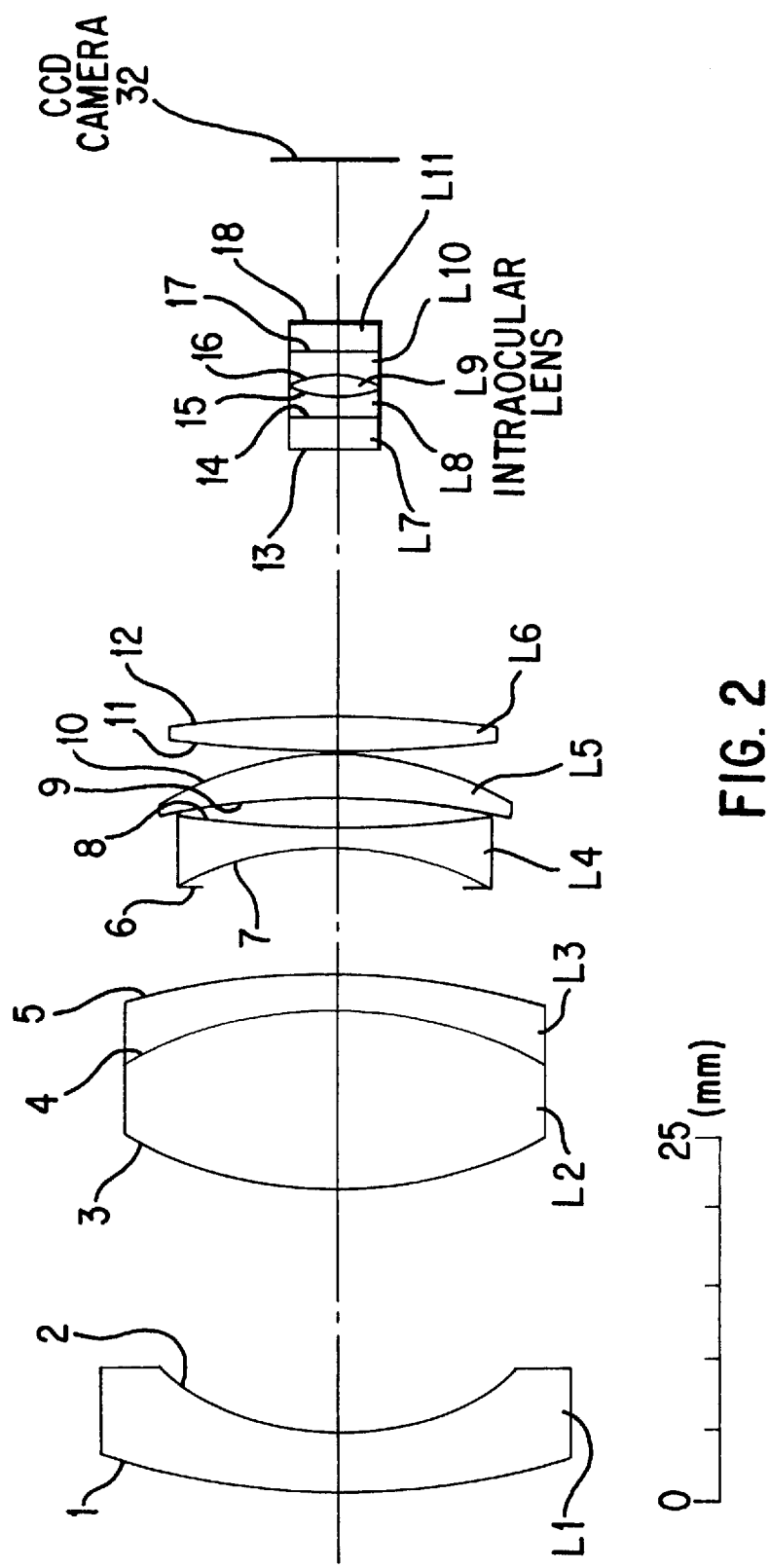
FIG. 2 is a cross-sectional detailed view of one embodiment of lens system according to the present invention.

FIG. 2 shows the detailed structure of the lens system 31 of one embodiment, which comprises, generally, a set of photographic lenses used as a model eye lens subsystem, an intraocular lens mounting section and an intraocular lens to be simulated.

In FIG. 2, first through sixth lenses L1 through L6 are a photographic lens assembly (compound lens), specifically, a retro-focus type wide angle photographic lens assembly (See, for example, the third embodiment in Japanese Patent Laid-Open No. 55-147607). If a single lens is used without using the wide angle photographic lens assembly, an image displayed on the display unit 33 turns out to be focused only at the center and blurred at other parts. That is, the use of the wide angle photographic lenses allows a clear image to be displayed on the whole display unit 33.

The seventh through eleventh lenses L7 through L11 are an intraocular lens mounting section with a simulated intraocular lens. The intraocular lens mounting section comprises at least a front lens L7 (on the side of the object 30) and a rear lens L11 (on the side of the display unit 33) which are glass plates capable of holding liquid, or some other substance which approximates the properties of the vitreous humor of the eye, between them. In this embodiment, water drums L8 and L10 are disposed between the plates L7 and L11. The simulated intraocular lens is supported between the liquid containing sections or water drums L8 and L10. According to the present embodiment, distilled water is filled in the water drums L8 and L10 of the intraocular lens mounting section. The liquid which may be filled in the water drums L8 and L10 is not confined only to distilled water. Aqueous humor or other liquid having refractive index close to that of the vitreous body of the eye may be used. The intraocular lens L9 is mounted within the water drums L8 and L10. An aperture not shown is attached in front of the intraocular lens L9 (on the subject side).

The position of the CCD camera 32 is set so that the CCD is positioned at an image point of the lens system 31.

The lens system 31 shown in FIG. 2 is designed so that an image of the subject at the point of infinity of the lens system 31 is formed by mounting an intraocular lens of +20D (diopter units) in the intraocular lens mounting section. A method of designing an intraocular lens using the system will be explained below.

Figure 3:
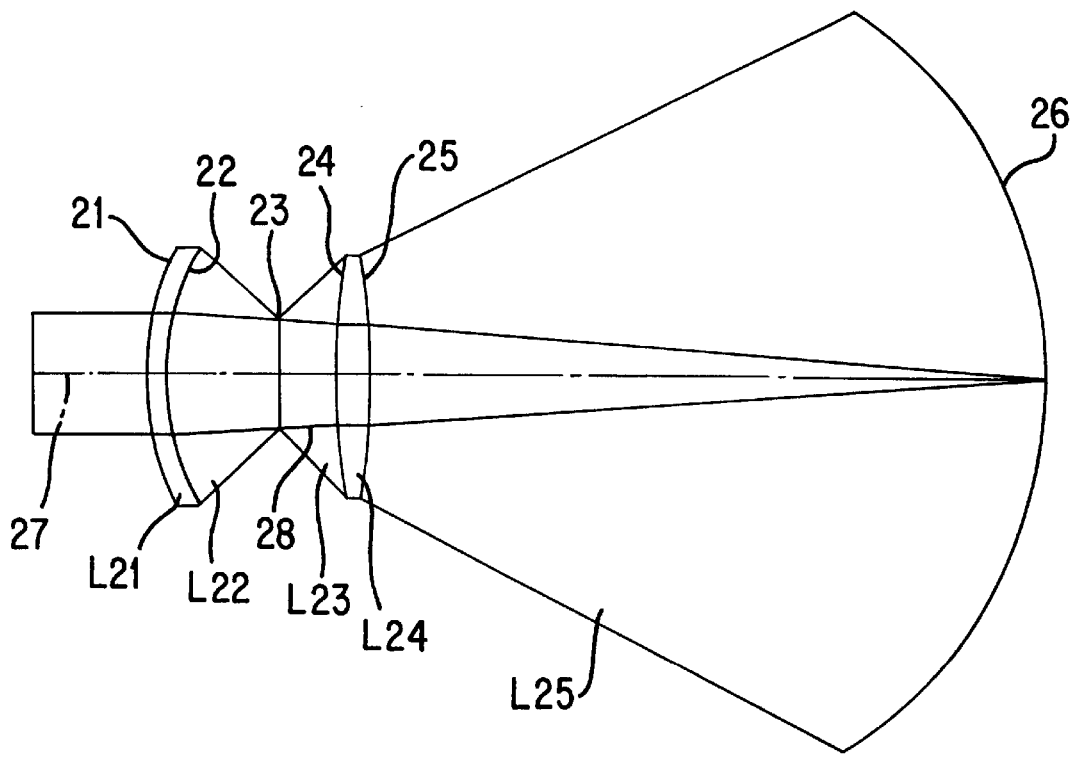
FIG. 3 shows a ray tracing diagram in which a crystal lens of Glustrand's ocular model is replaced with an intraocular lens according to an embodiment of the present invention.
Figure 4:
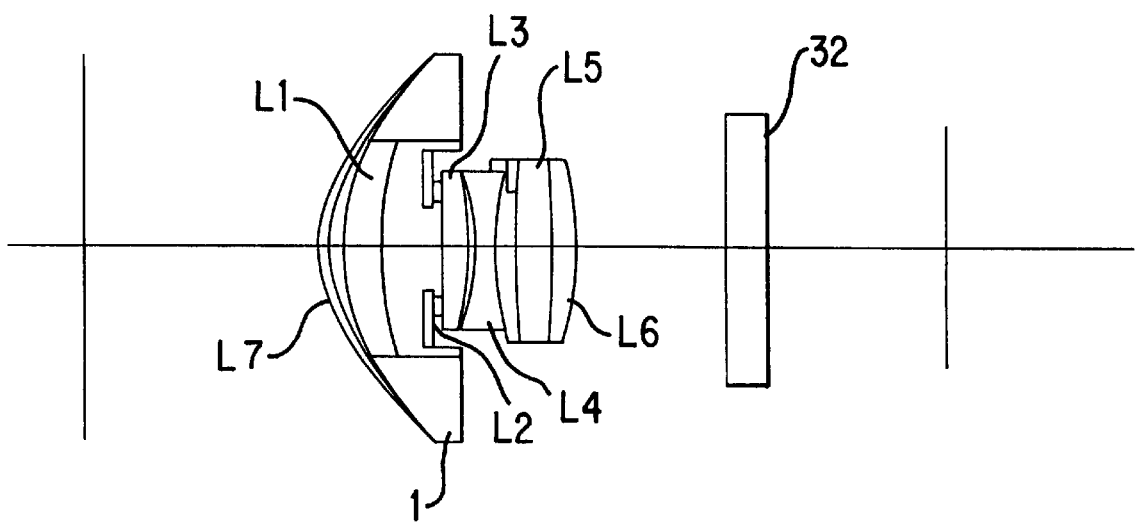
FIG. 4 shows the lens system according to another embodiment of the present invention in which the simulated lens is a contact lens.

FIG. 3 shows the results of a ray tracing diagram when the object is at the point of infinity obtained by replacing the crystalline lens of Glustrand's model eye with an intraocular lens of +20D. The optical system in FIG. 3 comprises five lenses L21 through L25. A face 26 corresponds in the model to the retina of the eye. Lens L1 between faces 21 and 22 corresponds to the cornea and face 23 corresponds to the iris. The lens L24 between faces 24 and 25 represents the intraocular lens of +20D.

Table 1 shows ray tracing data calculated from the optical system shown in FIG. 3. The wavelength used for calculation in this embodiment is 546.07 nm (E ray).

TABLE 1

| | Radius (mm) | Center Interval (mm) | Refractive Index | Distance of Paraxial Object Point (mm) |
|---|---|---|---|---|
| Face 21 | 7.70 | 0.50 | 1.3760 cornea | — |
| Face 22 | 6.80 | 3.10 | 1.3360 | 20.11 |
| Face 23 | iris | 1.40 | 1.3360 | 20.49 |
| Face 24 | 13.90 | 0.98 | 1.4930 IOL | 19.45 |
| Face 25 | −17.90 | | | 15.29 |

In the above Table 1, the radius is a radius of curvature of each lens face and the center interval is the distance between face vertexes, i.e. between each lens face and a lens face which precedes it by one (on the side of the retina 26).

The paraxial object point distance is a value generally defined as the distance from an object to a face vertex of each lens face. For example, the paraxial object point distance of front face 24 of the intraocular lens L24 in FIG. 3, is the distance from the intersection of a line extrapolated from line segment 28 and optical axis 27 to the face vertex. The face vertex of face 24 is the intersection of face 24 and optical axis 27.

The lens system 31 is designed so that the paraxial object point distance of the face 24 (the front refracting face of the intraocular lens L24) becomes equal to that of face 15 (the front refracting face of the intraocular lens L9) in FIG. 2.

Table 2 shows data of the faces 12 through 18 of the lens system 31 thus designed. The wavelength used in the calculations in this embodiment is 546.07 nm (E ray).

TABLE 2

| | Radius (mm) | Center Interval (mm) | Refractive Index | Distance of Paraxial Object Point (mm) |
|---|---|---|---|---|
| Face 12 | | 17.10 | Air | 77.61 |
| Face 13 | 0.00 | 2.00 | 1.51872 Parallel Plane Plate | 21.89 |
| Face 14 | 0.00 | 1.50 | 1.33600 (Water Drum) | 20.57 |
| Face 15 | 13.90 | 0.98 | 1.49300 IOL | 19.45 |
| Face 16 | −17.90 | 1.50 | 1.33600 (Water Drum) | 15.29 |
| Face 17 | 0.00 | 2.00 | 1.51872 (Parallel Plane Plate) | 12.36 |
| Face 18 | 0.00 | | Air | 11.70 |

In the above Table 2, the radius stated is the radius of curvature of each lens face and the center interval is the distance between face vertexes, i.e. between each lens face and the lens face that proceeds it by one (on the side of the retina 26). The paraxial object point distance is a value defined in the same manner as the paraxial object point distance in Table 1.

Comparing Table 1 with Table 2, it can be seen that the paraxial object point distance of the face 24 (the front refracting face of the intraocular lens L24 in FIG. 3) and that of the face 15 (the front refracting point of the intraocular lens L9 in FIG. 2) are both equal to 19.45 mm.

The use of ocular optical system simulation apparatus thus designed allows a retinal image of a subject or patient in whose eye the intraocular lens is implanted to be simulated by capturing the image of the object 30 by the CCD camera 32 via the lens system 31 and by displaying it on the display unit 33. The simulation can be implemented without redesigning the lens system, provided that the intraocular lens has the same diopter. When an intraocular lens having a different diopter needs to be accurately simulated, the simulation may be implemented by adjusting the position of the CCD camera 32 without redesigning the lens system. However, it may in some cases be necessary to design the lens system 31 in correspondence to the diopter. Furthermore, when an image of an object located at a point other than the point of infinity (neighboring vision or intermediate vision) is captured, the simulation can be implemented by adjusting the position of the CCD camera 32 without redesigning the lens system. Although it is also possible to redesign the lens system 31 to accomplish this end.

Even if the same intraocular lens is used, the size and clarity of an image may vary from person to person for two reasons: (1) the length of the axis of the eye differs from person to person, and (2) the shape of the cornea of the eye differs from person to person. Each of these properties can be measured, and accounted for in the process of the present invention by adjusting the relative position of the lens and the CCD camera, or alternatively by adjusting the diopter of the lens.

As described above, according to the present embodiment, because the simulation system is arranged such that the intraocular lens is mounted in the lens system, the image of the object is captured by the CCD camera and that image is displayed on the display unit, it becomes possible to simulate the retinal image when the intraocular lens is implanted. The patient and the doctor can thus readily evaluate the performance of the intraocular lens. Furthermore, the simulation can be used to closely approximate the state of an intraocular lens implanted in the human eye by mounting the intraocular lens within the water drums filled with distilled water.

The simulation apparatus also allows the patient and the doctor in charge who tries to implant the intraocular lens to know approximately how objects can be seen with the intraocular lens before implantation and to select the most suitable intraocular lens. Furthermore, not only the patient and the doctor in charge, but also designers and developers of intraocular lenses can readily evaluate and anticipate the performance of an intraocular lens.

The apparatus of the present invention allows evaluation of the performance of the intraocular lens in features such as color, flare, visual acuity, contrast and others.

Furthermore, it becomes possible to readily judge whether the implantation of the intraocular lens has been carried out properly or not by comparing, after implanting the intraocular lens, how things can be seen by the person to whom the intraocular lens has been implanted and how things can be seen when simulated by the inventive simulation system of ocular optical system.

The present invention is not confined only to the embodiment described above, and it may be modified in various ways.

It becomes possible to simulate various states by varying the diameter of the aperture attached in front of the intraocular lens or by varying an angle and position of the intraocular lens in mounting it. Specifically, when the angle and position of the intraocular lens to be mounted are varied, it becomes possible to check how the implantation has been carried out from the mounted position and angle of the intraocular lens showing the same image with the way how things can be seen by the patient to whom the intraocular lens has been implanted.

As described above, because the present invention is arranged such that the intraocular lens to be simulated is mounted in intraocular lens support, the lens system forms an image of the object, a pickup captures the image formed by the lens system and display means displays the image, it has become possible to simulate the retinal image that would be obtained when an intraocular lens is implanted in a human eye.

Contact Lens and Eyeglass Lens Simulation Embodiments

The general arrangement of the system according to the second embodiment is also shown in FIG. 1, and described above.

Next, a detailed structure of the lens system 31 will be described with respect to the embodiment in which the simulated lens is either a contact lens or an eyeglass lens.

FIG. 2 shows the detailed structure of the lens system 31, which generally comprises the model eye lens subsystem, a contact lens supporting base 1 and the contact lens L7 for performing a simulation.

In FIG. 2, the model eye lens subsystem is shown as comprising first lens L1 through sixth lens L6. The first lens L1, which is disposed at the nearest position to the object among the lenses comprising the lens system, is designed so that its first surface has substantially the same radius of curvature as that of the cornea of a human eye. When the contact lens to be simulated is a hard lens, its initial shape at wearing is maintained by filling a gap between the first lens L1 and the contact lens with distilled water. The distilled water makes a more accurate simulation possible by approximating human tears as well as making the contact lens maintain the initial shape during wear. The liquid filled between the first lens L1 and the contact lens is not limited to distilled water, but may comprise any liquid having a refractive index similar to that of tears.

The contact lens supporting base 1 is provided on the outer side of the first lens L1. The contact lens supporting base 1 corresponds to the conjunctiva of the human eye and the surface of the contact lens supporting base 1 opposite to the object is designed to have the same shape as the surface of the conjunctiva of the human eye. A soft contact lenses as well as a hard contact lenses may be used with the simulation apparatus of the present invention by providing a contact lens support base having substantially the same shape as that of the conjunctiva.

The pickup or CCD camera 32 is arranged such that it is positioned at an image point of the lens system 31.

An embodiment of the lens system 31 will be described below.

| | |
|---|---|
| Focal length (Referenced wave length e line: 546.07 nm) | 22.54 mm |
| Back focus | 16.93 mm (At INF) |
| FNo | 4.9 |
| Focusing method | Whole body screw in-out |
| Focusing distance | 3.6 mm to the object side (-6D 3.4252 mm) 2.9 mm to the image side (+6D 2.7460 mm) |
| Contact lens available | ±6.0D (Preferably within ±3.0D) |

Next, detailed data concerning the lens system will be shown in Table 1.

TABLE 1

| Surface | Radius of curvature | Distance between surfaces | Nd | vd |
|---|---|---|---|---|
| L1 1 | 7.72 | 1.70 | 1.49700 | 81.6 |
| L1 2 | 12.90 | 2.11 | | |
| L2 | diaphragm | 0.20 | | |
| L3 1 | 39.10 | 1.40 | 1.71300 | 53.9 |
| L3 2 | -15.60 | 0.54 | | |
| L4 1 | -9.50 | 1.00 | 1.62588 | 35.7 |
| L4 2 | 10.50 | 1.00 | | |
| L5 1 | 22.70 | 1.50 | 1.80610 | 38.3 |
| L6 1 | -54.80 | 1.23 | 1.49700 | 81.6 |
| L6 2 | -13.74 | 16.93 | | |

The above-mentioned lens system 31 is designed such that the first surface of the first lens L1 has substantially the same radius of curvature as that of the cornea of the human eye. By means of ray tracing, the aberration is reduced when a ±6D contact lens is attached. For example, with a ±6D lens, a worsening of the modulation transfer function is seen at a peripheral field half-angle of 5.5° due to astigmatic aberration. However, if, for example, a CCD camera with a picture element on the order of 10 micron is used and the modulation transfer function calculated according to a given spatial frequency with 100 lines/mm, a modulation transfer function of greater than 25% is obtained, which is sufficient for the simulation. Even though, in the present embodiment, the lens system is designed such that the aberration is reduced in the range of ±6D, yet smaller aberrations suitable for the simulation can be obtained with lenses having diopters in the range of ±3D.

The simulation apparatus for an ocular optical system thus designed can simulate the retinal image of a patient wearing a contact lens by picking up the object 30 by means of the CCD camera 32 through the lens system 31 and by displaying the image on the display device 33. The relative position between the lens system 31 and the CCD camera 32 can be adjusted in the ocular optical system simulation apparatus according to the present invention. Adjusting the relative positions of the lens system 31 and the CCD camera 32 makes it possible to have a simulation in which the image of an object is picked up not only at infinity, but also at close or intermediate proximity.

As mentioned above, since the simulation apparatus according to the above-mentioned embodiment is designed such that the CCD camera picks up the image of the object with a contact lens attached to the lens system and the image is displayed on the display device, simulating the retinal image when the contact lens is worn becomes possible so that the patient and the doctor can easily evaluate performance of the lens on the eye. Furthermore, the contact lens supporting base provided in the system makes it easy to attach and detach the simulated contact lens.

Lens performance can be evaluated by color, flare, visual acuity, contrast and the like. Particularly, a multi-focal lens can be easily simulated and multi-focal contact lenses can be effectively tested and developed.

The above described embodiment concerns the case when the present invention is applied to simulate and test a contact lens. However, the present invention can be also applied to an eyeglass lens. When the present invention is applied to an eyeglass lens, the contact lens L7 is replaced by an eyeglass lens, which is disposed apart from the lens L1 at a distance approximating the distance between an eye and an eyeglass lens when eyeglasses are worn.

Though the contact lens supporting base shown in the above embodiment is made of glass, the material other than glass, for example metal, may also be used.

Furthermore, devices other than a CCD camera may be used for picking up the image from the lens system. For example, a device for picking up monochrome image only may also be used, if desired.

As explained above, according to the present invention, the lens system focuses the image of the object with the contact lens or eyeglass lens attached, and the image pickup picks up the image focused by the lens system. Accordingly, it is possible to simulate the retinal image that would be obtained when a contact lens, or eyeglass lens is worn on a human eye.

While the present invention has been illustrated by means of several preferred embodiments, one of ordinary skill in the art will recognize that modifications, substitutions and improvements may be made while staying within the spirit and scope of invention as recited in the appended claims.

What is claimed is:

1. An apparatus for simulating a retinal image when a lens is used with a human eye, comprising:
    a lens system having a model eye lens subsystem and a simulated lens; and
    an image pickup for picking up an image of an object focused by said lens system.

2. An apparatus according to claim 1, wherein said simulated lens is an intraocular lens, and wherein said lens system further comprises:
    an intraocular lens support for supporting the intraocular lens; and
    a compound lens member optically connected to the intraocular lens support, whereby the compound lens and intraocular lens support are constructed so that said image substantially reproduces a retinal image obtained when the intraocular lens had been implanted in a human eye.

3. An apparatus according to claim 2, wherein said compound lens member is a wide angle lens.

4. An apparatus according to claim 3, wherein said wide angle lens is disposed between said object and said intraocular lens support.

5. The apparatus according to claim 2, wherein said intraocular lens supporting means comprises a liquid containing section and said intraocular lens is supported in liquid disposed in the liquid containing section.

6. An apparatus according to claim 2, further comprising a display connected to said image pickup for displaying said image.

7. An apparatus according to claim 2, wherein said simulated intraocular lens has a front face facing said object with a paraxial object point distance substantially equal to a paraxial object point distance of a front face of said intraocular lens when implanted in a human eye.

8. An apparatus according to claim 2, wherein the simulated interocular lens has a front face facing said object with a paraxial object point distance substantially equal to a paraxial object point distance of an intraocular lens of equal diopter used to replace a crystalline lens in Glustrand's ocular model.

9. An apparatus according to claim 2, wherein said image pickup comprises a charge coupled device camera.

10. An apparatus according to claim 1, wherein said simulated lens is a simulated contact lens; and wherein the model eye subsystem comprises a simulated cornea lens having a first surface disposed at a position nearest to said object in said model eye lens subsystem, wherein the first surface has a radius of curvature substantially corresponding to a radius of curvature of the cornea of a human eye.

11. An apparatus according to claim 10, wherein a liquid is disposed between said first surface of said simulated cornea lens and said simulated contact lens, thereby supporting said contact lens.

12. An apparatus according to claim 10, further comprising a contact lens support base provided outside of an outer periphery of said simulated cornea lens, and a liquid provided between said contact lens support base and said simulated contact lens to support said contact lens.

13. An apparatus according to claim 12, wherein at least a part of said contact lens support base has a shape corresponding to a conjunctiva of a human eye.

14. An apparatus according to claim 10, further comprising a display connected to said image pickup for displaying said image.

15. An apparatus according to claim 10, wherein said image pickup comprises a charge coupled device camera.

16. An apparatus according to claim 1, wherein said simulated lens is an eyeglass lens, and further comprising a support for supporting said eyeglass lens at a predetermined position with respect to said model eye lens subsystem.

* * * * *